United States Patent
Carlson et al.

(10) Patent No.: US 7,069,070 B2
(45) Date of Patent: Jun. 27, 2006

(54) STATISTICAL METHOD FOR ASSESSING AUTONOMIC BALANCE

(75) Inventors: Gerrard M. Carlson, Champlin, MN (US); Ronald D. Berger, Baltimore, MD (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 498 days.

(21) Appl. No.: 10/436,876

(22) Filed: May 12, 2003

(65) Prior Publication Data

US 2004/0230241 A1 Nov. 18, 2004

(51) Int. Cl.
*A61B 5/0452* (2006.01)

(52) U.S. Cl. .................. 600/519; 600/513; 600/509

(58) Field of Classification Search ............... 600/509, 600/481, 513, 519, 521
See application file for complete search history.

(56) References Cited

U.S. PATENT DOCUMENTS

| | | |
|---|---|---|
| 4,114,627 A | 9/1978 | Lewyn et al. |
| 4,777,960 A | 10/1988 | Berger et al. |
| 4,791,931 A | 12/1988 | Slate |
| 4,872,459 A | 10/1989 | Pless et al. |
| 4,880,005 A | 11/1989 | Pless et al. |
| 4,945,909 A | 8/1990 | Fearnot et al. |
| 5,014,698 A | 5/1991 | Cohen |
| 5,063,927 A | 11/1991 | Webb et al. |
| 5,111,815 A | 5/1992 | Mower |
| 5,183,040 A | 2/1993 | Nappholz et al. |
| 5,190,035 A | 3/1993 | Salo et al. |
| 5,197,467 A | 3/1993 | Steinhaus et al. |
| 5,199,428 A | 4/1993 | Obel et al. |
| 5,201,808 A | 4/1993 | Steinhaus et al. |
| 5,203,326 A | 4/1993 | Collins |
| 5,222,493 A | 6/1993 | Sholder |
| 5,243,980 A | 9/1993 | Mehra |
| 5,269,301 A | 12/1993 | Cohen |
| 5,271,395 A | 12/1993 | Wahlstrand et al. |
| 5,273,034 A | 12/1993 | Nilsson |
| 5,291,400 A | 3/1994 | Gilham |
| 5,300,093 A | 4/1994 | Koestner et al. |
| 5,303,702 A | 4/1994 | Bonnet et al. |
| 5,318,592 A | 6/1994 | Schaldach |

(Continued)

FOREIGN PATENT DOCUMENTS

EP    0555988 A2    8/1993

(Continued)

OTHER PUBLICATIONS

"Heart Rate Variability: Standards of Measurement, Physiological Interpretation, and Clinical Use", *European Heart Journal*, 17, Prepared by the Task Force of The European Society of Cardiology and The North American Society of Pacing and Electrophysiology; published by the American Heart Association, Inc.; European Society of Cardiology,(1996),pp. 354-381.

(Continued)

*Primary Examiner*—Kennedy Schaetzle
(74) *Attorney, Agent, or Firm*—Schwegman, Lundberg, Woessner & Kluth, P.A.

(57) ABSTRACT

A computationally efficient method for assessing a subject's autonomic balance by measurement of heart rate variability is disclosed which is particularly suitable for implementation by an implantable medical device. Statistical surrogates are used to represent frequency components of an RR time series. A ratio of the low frequency component to the high frequency component may then be estimated to assess the subject's autonomic balance.

20 Claims, 2 Drawing Sheets

U.S. PATENT DOCUMENTS

| | | | |
|---|---|---|---|
| 5,318,597 A | 6/1994 | Hauck et al. | |
| 5,324,310 A | 6/1994 | Greeninger et al. | |
| 5,330,507 A | 7/1994 | Schwartz | |
| 5,331,966 A | 7/1994 | Bennett et al. | |
| 5,341,811 A | 8/1994 | Cano | |
| 5,356,425 A | 10/1994 | Bardy et al. | |
| 5,360,436 A | 11/1994 | Alt et al. | |
| 5,391,190 A | 2/1995 | Pederson et al. | |
| 5,411,531 A | 5/1995 | Hill et al. | |
| 5,423,870 A | 6/1995 | Olive et al. | |
| 5,431,687 A | 7/1995 | Kroll | |
| 5,431,693 A | 7/1995 | Schroeppel | |
| 5,437,285 A | 8/1995 | Verrier et al. | |
| 5,441,524 A | 8/1995 | Rueter et al. | |
| 5,443,485 A | 8/1995 | Housworth et al. | |
| 5,466,245 A | 11/1995 | Spinelli et al. | |
| 5,480,412 A | 1/1996 | Mouchawar et al. | |
| 5,507,784 A | 4/1996 | Hill et al. | |
| 5,507,785 A | 4/1996 | Deno | |
| 5,522,854 A | 6/1996 | Ideker et al. | |
| 5,531,772 A | 7/1996 | Prutchi | |
| 5,560,370 A | 10/1996 | Verrier et al. | |
| 5,562,711 A | 10/1996 | Yerich et al. | |
| 5,562,712 A | 10/1996 | Steinhaus et al. | |
| 5,571,144 A | 11/1996 | Schroeppel | |
| 5,578,061 A | 11/1996 | Stroetmann et al. | |
| 5,601,615 A | 2/1997 | Markowitz et al. | |
| 5,603,331 A | 2/1997 | Heemels et al. | |
| 5,626,622 A | 5/1997 | Cooper | |
| 5,626,624 A | 5/1997 | Schaldach et al. | |
| 5,645,570 A | 7/1997 | Corbucci | |
| 5,658,318 A | 8/1997 | Stroetmann et al. | |
| 5,682,901 A | 11/1997 | Kamen | |
| 5,685,316 A | 11/1997 | Schookin et al. | |
| 5,690,681 A | 11/1997 | Geddes et al. | |
| 5,700,282 A | 12/1997 | Zabara | |
| 5,700,283 A | 12/1997 | Salo | |
| 5,718,720 A | 2/1998 | Prutchi et al. | |
| 5,722,997 A | 3/1998 | Nedungadi et al. | |
| 5,749,900 A | 5/1998 | Schroeppel et al. | |
| 5,755,671 A | 5/1998 | Albrecht et al. | |
| 5,766,225 A | 6/1998 | Kramm | |
| 5,782,884 A | 7/1998 | Stotts et al. | |
| 5,792,194 A | 8/1998 | Morra | |
| 5,817,135 A | 10/1998 | Cooper et al. | |
| 5,817,136 A | 10/1998 | Nappholz et al. | |
| 5,824,020 A | 10/1998 | Cooper | |
| 5,824,029 A | 10/1998 | Weijand et al. | |
| 5,842,997 A | 12/1998 | Verrier et al. | |
| 5,843,136 A | 12/1998 | Zhu et al. | |
| 5,861,012 A | 1/1999 | Stroebel | |
| 5,873,898 A | 2/1999 | Hemming et al. | |
| 5,891,044 A | 4/1999 | Golosarsky et al. | |
| 5,893,882 A | 4/1999 | Peterson et al. | |
| 5,916,239 A | 6/1999 | Geddes et al. | |
| 5,921,940 A | 7/1999 | Verrier et al. | |
| 5,935,081 A | 8/1999 | Kadhiresan | |
| 5,941,831 A | 8/1999 | Turcott | |
| 5,978,707 A | 11/1999 | Krig et al. | |
| 5,978,710 A | 11/1999 | Prutchi et al. | |
| 5,987,356 A | 11/1999 | DeGroot | |
| 6,006,134 A | 12/1999 | Hill et al. | |
| 6,021,351 A | 2/2000 | Kadhiresan et al. | |
| 6,022,322 A | 2/2000 | Prutchi | |
| 6,026,320 A | 2/2000 | Carlson et al. | |
| 6,035,233 A | 3/2000 | Schroeppel et al. | |
| 6,042,548 A | 3/2000 | Giuffre | |
| 6,044,294 A | 3/2000 | Mortazavi et al. | |
| 6,058,331 A | 5/2000 | King | |
| 6,073,048 A | 6/2000 | Kieval et al. | |
| 6,076,015 A | 6/2000 | Hartley et al. | |
| 6,128,535 A | 10/2000 | Maarse | |
| 6,134,470 A | 10/2000 | Hartlaub | |
| 6,135,970 A | 10/2000 | Kadhiresan et al. | |
| 6,144,878 A | 11/2000 | Schroeppel et al. | |
| 6,151,524 A | 11/2000 | Krig et al. | |
| 6,161,042 A | 12/2000 | Hartley et al. | |
| 6,178,349 B1 | 1/2001 | Kieval | |
| 6,181,966 B1 | 1/2001 | Nigam | |
| 6,216,032 B1 | 4/2001 | Griffin et al. | |
| 6,224,553 B1 | 5/2001 | Nevo | |
| 6,240,314 B1 | 5/2001 | Plicchi et al. | |
| 6,246,909 B1 | 6/2001 | Ekwall | |
| 6,269,263 B1 | 7/2001 | Ohnishi et al. | |
| 6,272,377 B1 | 8/2001 | Sweeney et al. | |
| 6,273,856 B1 | 8/2001 | Sun et al. | |
| 6,292,695 B1 | 9/2001 | Webster, Jr. et al. | |
| 6,301,499 B1 | 10/2001 | Carlson et al. | |
| 6,317,632 B1 | 11/2001 | Krig et al. | |
| 6,358,201 B1 | 3/2002 | Childre et al. | |
| 6,370,424 B1 | 4/2002 | Prutchi | |
| 6,371,922 B1 | 4/2002 | Baumann et al. | |
| 6,390,986 B1 | 5/2002 | Curcie et al. | |
| 6,400,982 B1 | 6/2002 | Sweeney et al. | |
| 6,421,557 B1 | 7/2002 | Meyer | |
| 6,438,421 B1 | 8/2002 | Stahmann et al. | |
| 6,449,507 B1 | 9/2002 | Hill et al. | |
| 6,453,201 B1 | 9/2002 | Daum et al. | |
| 6,459,929 B1 | 10/2002 | Hopper et al. | |
| 6,463,326 B1 | 10/2002 | Hartley et al. | |
| 6,470,210 B1 | 10/2002 | Chen et al. | |
| 6,473,644 B1 | 10/2002 | Terry, Jr. et al. | |
| 6,480,733 B1 | 11/2002 | Turcott | |
| 6,480,742 B1 | 11/2002 | Stahmann et al. | |
| 6,487,450 B1 | 11/2002 | Chen et al. | |
| 6,493,585 B1 | 12/2002 | Plicchi et al. | |
| 6,511,500 B1 | 1/2003 | Rahme | |
| 6,522,914 B1 | 2/2003 | Huvelle | |
| 6,522,926 B1 | 2/2003 | Kieval et al. | |
| 6,529,772 B1 | 3/2003 | Carlson et al. | |
| 6,532,388 B1 | 3/2003 | Hill et al. | |
| 6,542,774 B1 | 4/2003 | Hill et al. | |
| 6,564,096 B1 | 5/2003 | Mest | |
| 6,571,121 B1 | 5/2003 | Schroeppel et al. | |
| 6,571,122 B1 | 5/2003 | Schroeppel et al. | |
| 6,611,713 B1 | 8/2003 | Schauerte | |
| 6,622,041 B1 | 9/2003 | Terry, Jr. et al. | |
| 6,628,987 B1 | 9/2003 | Hill et al. | |
| 6,647,289 B1 | 11/2003 | Prutchi | |
| 6,678,547 B1 * | 1/2004 | Carlson et al. | 600/515 |
| 6,690,971 B1 | 2/2004 | Schauerte et al. | |
| 6,824,538 B1 | 11/2004 | Chen | |
| 6,850,801 B1 | 2/2005 | Kieval et al. | |
| 6,856,829 B1 | 2/2005 | Ohsaki et al. | |
| 2002/0058877 A1 | 5/2002 | Baumann et al. | |
| 2002/0107552 A1 | 8/2002 | Krig et al. | |
| 2002/0107553 A1 | 8/2002 | Hill et al. | |
| 2002/0123768 A1 | 9/2002 | Gilkerson | |
| 2002/0123769 A1 | 9/2002 | Panken et al. | |
| 2002/0143369 A1 | 10/2002 | Hill et al. | |
| 2002/0161410 A1 | 10/2002 | Kramer et al. | |
| 2002/0165586 A1 | 11/2002 | Hill et al. | |
| 2003/0003052 A1 | 1/2003 | Hampton | |
| 2003/0004549 A1 | 1/2003 | Hill et al. | |
| 2003/0045909 A1 | 3/2003 | Gross et al. | |
| 2003/0060857 A1 | 3/2003 | Perrson et al. | |
| 2003/0069609 A1 | 4/2003 | Thompson | |
| 2003/0078623 A1 | 4/2003 | Weinberg et al. | |
| 2003/0093002 A1 * | 5/2003 | Kuo | 600/528 |
| 2003/0100924 A1 | 5/2003 | Foreman et al. | |
| 2003/0105493 A1 | 6/2003 | Salo et al. | |
| 2003/0114889 A1 | 6/2003 | Huvelle et al. | |
| 2003/0135126 A1 | 7/2003 | Kuo | |
| 2003/0149450 A1 | 8/2003 | Mayberg | |

| | | | |
|---|---|---|---|
| 2003/0212440 | A1 | 11/2003 | Boveja |
| 2004/0019289 | A1* | 1/2004 | Ross .......................... 600/519 |
| 2004/0093035 | A1 | 5/2004 | Schwartz et al. |
| 2004/0102908 | A1 | 5/2004 | Larson et al. |
| 2004/0116820 | A1 | 6/2004 | Daum et al. |
| 2004/0133247 | A1 | 7/2004 | Stahmann et al. |
| 2004/0158295 | A1 | 8/2004 | Dyjach et al. |
| 2005/0065554 | A1 | 3/2005 | KenKnight et al. |

FOREIGN PATENT DOCUMENTS

| | | |
|---|---|---|
| EP | 0709058 A1 | 1/1996 |
| EP | 0709112 A2 | 5/1996 |
| WO | WO-94/06350 A1 | 3/1994 |
| WO | WO-94/15319 A1 | 4/1998 |
| WO | WO-98/15319 A1 | 4/1998 |
| WO | WO-00/04950 A2 | 2/2000 |
| WO | WO-00/38782 A1 | 7/2000 |
| WO | WO-00/44274 A2 | 8/2000 |
| WO | WO-00/51680 A1 | 9/2000 |

OTHER PUBLICATIONS

"International Search Report for PCT Application No. PCT/US2004/031062",(Feb. 17, 2005),5 pgs.

Behrens, S., "Effects of Amiodarone on the Circadian Pattern of Sudden Cardiac Death (Department of Vererans Affairs Congestive Heart Failure-Survival Trial of Antiarrhythmic Therapy)", *Am. J. Cardiol.*, 80(1), (Jul. 1997),45-48.

Behrens, S. S., "Modification of the Circadian Pattern of Ventricular Tachyarrhythmias by Beta-Blocker Therapy", *Clin, Cardiol.*, 20(3), (Mar. 1997),253-257.

Berger, R. D., "An Efficient Algorithm for Spectral Analysis of Heart Rate Variability", *IEEE Transactions on Biomedical Engineering, BME-33 (9)*, (Sep. 1986),900-904.

Bigger, J. T., "Correlations Among Time and Frequency Domain Measures of Heart Period Variability Two Weeks After Acute Myocardial Infarction", *Arrhythmias and Conduction Disturbances*, 69, (Apr. 1, 1992),891-898.

Bigger, Jr., J. T., "Spectral Analysis of R-R Variability to Evaluate Autonomic Physiology and Pharmacology and to Predict Cardiovascular Outcomes in Humans", *Am. J. Cardiol.*, 69(9), (Apr. 1, 1992),891-898.

Libbus, I. , "Combined Remodeling Control Therapy and Anti-Remodeling Therapy By Implantable Cardiac Device", U.S. Appl. No. 10/850,341, filed May 20, 2004, 25 pgs.

No Authors Listed, "Heart rate variability: standards of measurement, physiological interpretation and clinical use. Task Force of the European Society of Cardiology and the North American Society of Pacing and Electrophysiology", *Circulation*, 93(5), (Mar. 1, 1996), 1043-1065.

Scheiner, A. , et al., "System and Method for Monitoring Autonomic Balance and Physical Activity", U.S. Appl. No. 10/695,430, filed Oct. 28, 2003, 20 pgs.

* cited by examiner

STATISTICAL METHOD FOR ASSESSING AUTONOMIC BALANCE

FIELD OF THE INVENTION

This invention pertains to cardiac rhythm management devices such as pacemakers and implantable monitoring devices.

BACKGROUND

Heart rate variability (HRV) refers to the changes in the length of time between consecutive heart beats during sinus rhythm and is primarily due to the interaction between the sympathetic and parasympathetic arms of the autonomic nervous system. Measurement and analysis of heart rate variability is thus a useful and non-invasive tool for assessing the status of the autonomic nervous system.

A heart beat is usually measured as the time from the peak of one R wave to the peak of the next, referred to as an RR interval. The variability of normal RR intervals (i.e., during sinus rhythm) can be determined and analyzed in several different ways in either the time domain or the frequency domain. Time domain measurements involve the computation of a statistic based upon the individual RR intervals making up an RR time series such as the standard deviation of the RR intervals in the series. Frequency domain analysis, on the other hand, employs methods such as the Fast Fourier Transform (FFT) or autoregressive analysis to analyze the frequency spectrum of the variability in the RR intervals. This latter type of analysis has proven to be particularly valuable in assessing the relative activities of the sympathetic and parasympathetic nervous systems in a subject. Such assessment of the state of autonomic balance would be a useful function for implantable cardiac rhythm management devices such as pacemakers and implantable cardioverter/defibrillators to perform as it could be used to modify the manner in which therapy is delivered by the device or to predict the occurrence of arrhythmias. Frequency domain analysis of heart rate variability, however, requires computational and data storage capabilities that may not be practical in present-day implantable devices.

SUMMARY

The present invention is a method for assessing the autonomic balance of a subject by estimating the ratio of certain frequency components in an RR time series based upon statistics computed from the RR intervals making up the series. The method is especially suitable for use by an implantable device since the required statistics may be computed without the processing overhead and data storage capability associated with frequency domain analysis. The statistics used to estimate the frequency component ratio may be computed by cumulatively summing particular functions of RR interval measurements or by a histogram technique in which the relative frequencies of RR interval values or functions thereof are calculated from running counts of the RR interval measurements whose values are within specified ranges.

DETAILED DESCRIPTION

As noted above, heart rate variability refers to the variability of the time intervals between successive heart beats during a sinus rhythm. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. If an implantable medical device could monitor the LF/HF ratio, the device could log a clinically significant event when the ratio exceeds a specified threshold value, as well as possibly automatically altering its mode of operation (e.g., initiating different therapies or performing more computationally intensive data analysis for arrhythmia prediction).

A series of RR interval values can be regarded as a discrete signal indexed by heartbeat such that each value of the signal represents an RR interval for a particular heartbeat. In order to properly analyze the frequency content of heart rate variability, however, the RR time series should be resampled at a specified sampling frequency in order to equalize the time intervals between interval values and thus convert the time series into a discrete time signal, where the sampling frequency is selected to meet the Nyquist criterion with respect to the frequencies of interest. Spectral analysis of such an RR interval signal can then be performed directly in the frequency domain using discrete Fourier transform or autoregression techniques in order to compute the LF/HF ratio. A time-domain technique for determining the high and low frequency components of the signal could also be used in which the RR interval signal is input to low band and high band digital filters and signals proportional to the power of the RR interval signal in each of the low frequency and high frequency bands are derived so that the LF/HF ratio may be computed. Both frequency domain and time domain analysis performed in this manner are computationally intensive, however, and require the storage of large amounts of RR interval data. Such methods may therefore not be practical in a typical implantable medical device which is a small battery-powered device with limited processing power. As described below, statistical techniques that do not involve such processing overhead may be used to generate surrogate parameters from which the LF/HF ratio may be calculated.

1. Exemplary Implantable Device Description

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Cardiac rhythm management devices may also treat tachyarrhythmias, where the heart rate is too fast, by anti-tachycardia pacing and/or delivery of defibrillation shocks. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

Figure 1:
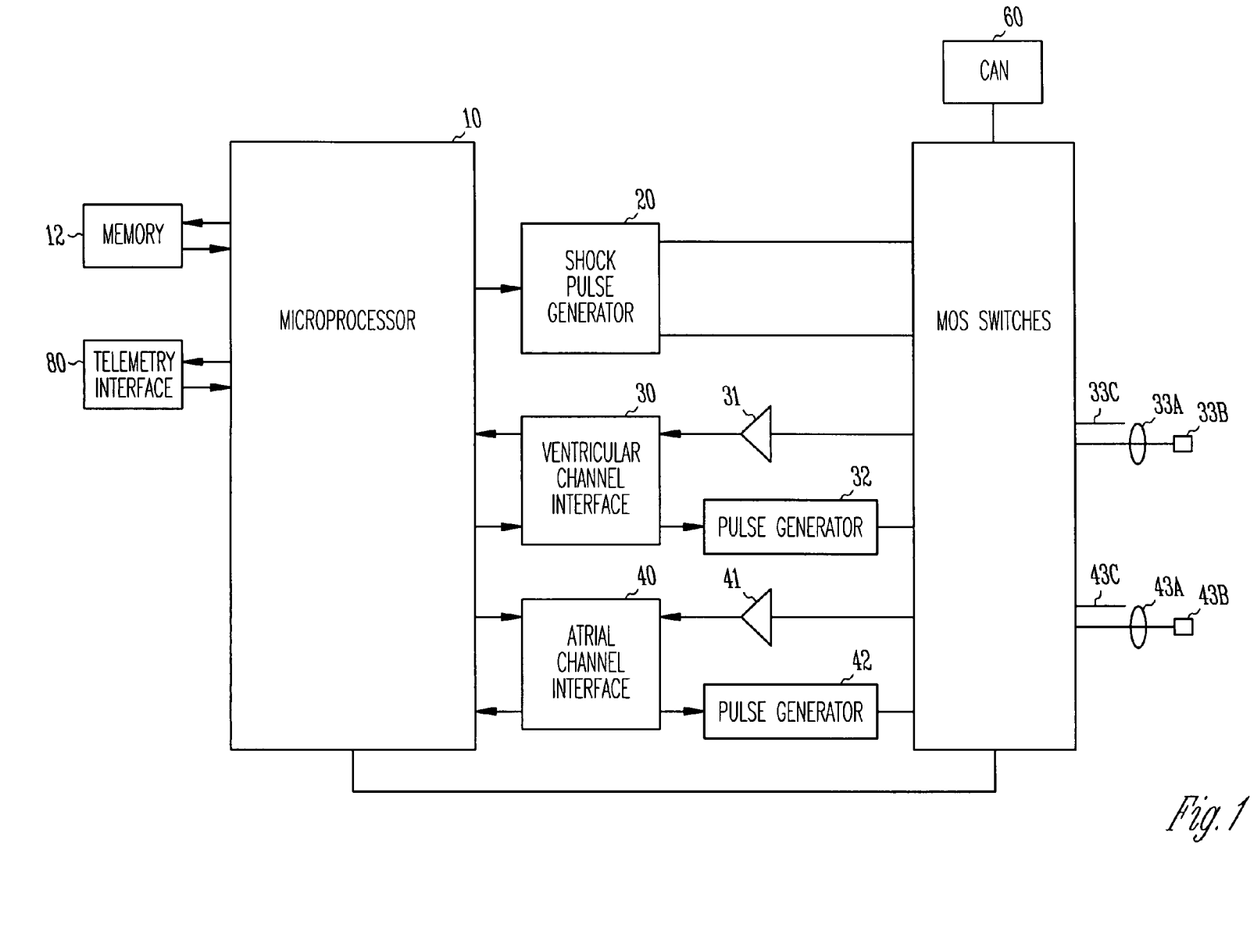
FIG. 1 is a block diagram of an exemplary cardiac rhythm management device for practicing the present invention.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer.

The embodiment shown in FIG. 1 has two sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. The channels may be configured as either atrial or ventricular channels. In an example configuration, an atrial sensing/pacing channel includes ring electrode 43a and tip electrode 43b of bipolar lead 43c, sense amplifier 41, pulse generator 42, and a channel interface 40. A ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator 20 is also interfaced to the controller for delivering defibrillation shocks through electrodes selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing. The switch matrix 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels in order to control the delivery of paces in accordance with a pacing mode and/or deliver shock therapy in response to detection of a tachyarrhythmia such as ventricular fibrillation. The sensing circuitry of the device generates atrial and ventricular electrogram signals from the voltages sensed by the electrodes of a particular channel. An electrogram is analogous to a surface ECG and indicates the time course and amplitude of cardiac depolarization that occurs during either an intrinsic or paced beat. When an electrogram signal in an atrial or sensing channel exceeds a specified threshold, the controller detects an atrial or ventricular sense, respectively, which pacing algorithms may employ to trigger or inhibit pacing and from which heart rates may be derived by measuring the intervals between senses.

2. Statistical Assessment of Autonomic Balance

A cardiac rhythm management device such as illustrated in FIG. 1 can be programmed to determine heart rate variability by analyzing data received from its ventricular sensing channels. The intervals between successive ventricular senses, referred to as RR intervals, can be measured for a specified period of time or a specified number of beats and their variability analyzed. A typical RR time series, for example, would be made up of RR intervals over 24 hours or other long-term period. In order to derive a signal representing heart rate variability during a sinus rhythm, ectopic ventricular beats (i.e., premature ventricular contractions or PVCs) can be detected by monitoring whether a P wave precedes each R wave, with the RR intervals before and after the PVC changed to an interpolated or otherwise filtered value. An RR interval signal collected in this manner could be spectrally analyzed by the device in order to determine the frequency content in the LF and HF bands by either transforming the signal into the frequency domain or by decomposing the signal with bandpass filters. Both of these approaches, however, require extensive calculations and the storage of large amounts of data. A less computationally intensive way of spectrally analyzing an RR time series is to employ certain statistical parameters as surrogates for the actual specific frequency components.

Figure 2A:
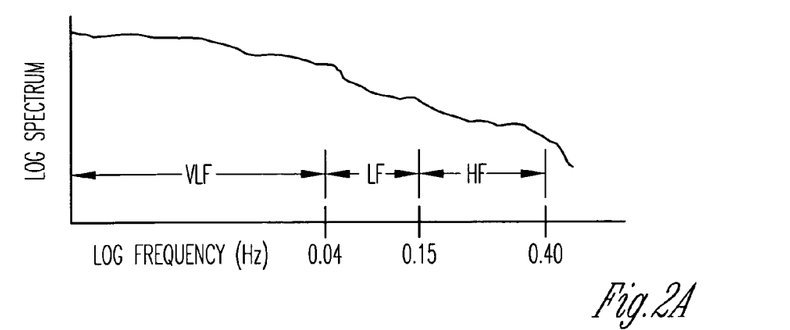
FIGS. 2A through 2D illustrate an exemplary spectrum of an RR time series and the frequency responses represented by statistical surrogates.
Figure 2B:
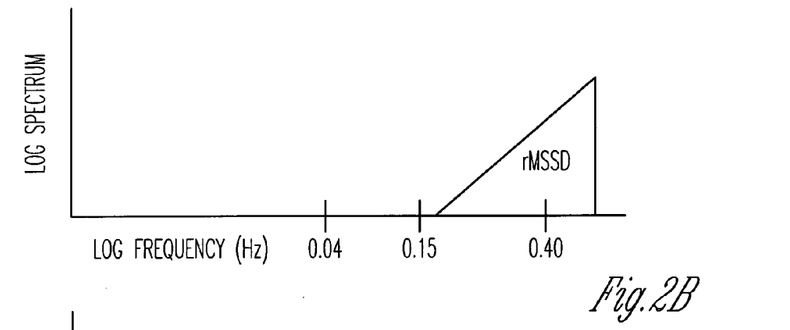
Figure 2C:
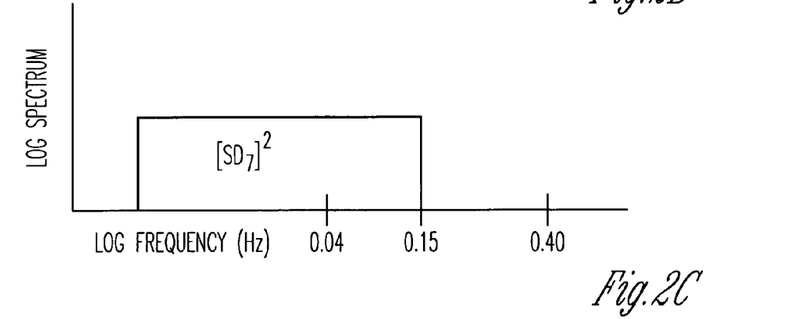
Figure 2D:
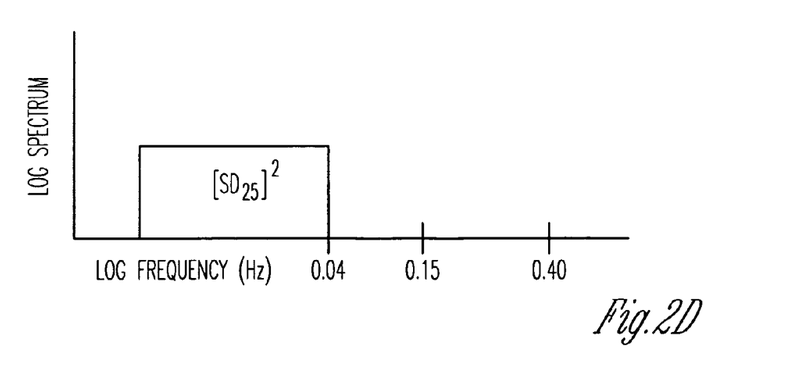

FIG. 2A illustrates a log frequency plot of the spectrum an example RR time series showing a very low frequency component VLF between DC (i.e., no variability in the RR intervals) and 0.04 Hz, a low frequency component LF between 0.04 Hz and 0.15 Hz, and a high frequency component HF between 0.15 and 0.40 Hz. FIGS. 2B through 2D illustrate how the frequency components of an RR time series would be reflected by different statistical parameters. The rMSSD statistic is defined as the square root of the mean of the squared successive differences of an RR time series:

$$rMSSD = E\{(RR_i - RR_{i-1})^2\}^{0.5}$$

where E is the expectation or mean value operator, and $RR_i$ refers to the ith RR interval in the series. The square root step in the calculation can be omitted to give the $[rMSSD]^2$ parameter. By averaging the square of the successive interval-to-interval difference values in the RR time series, the rMSSD or $[rMSSD]^2$ statistic maximally reflects variations in the RR intervals that occur with each successive interval and progressively attenuates variations in the RR intervals that occur at lower frequencies. The frequency response represented by the rMSSD statistic shown in FIG. 2B is therefore greatest at the maximum frequency that can be represented in the time series (i.e., approximately one-half of the average heart rate, similar to the Nyquist frequency in a time series with regular intervals) and then decreases linearly with decreasing frequency so that lower frequency variability in the RR time series is not represented. Computation of the rMSSD or $[rMSSD]^2$ statistic thus captures a frequency range of heart rate variability which is similar to the HF band illustrated in FIG. 2A.

The $SD_7$ statistic is defined as the standard deviation of the mean values of all successive 7-second segments in the RR time series, and $[SD_7]^2$ is the square of that standard deviation or variance. By computing mean values of the RR intervals over 7-second segments, the $[SD_7]^2$ statistic averages out the variations in the RR intervals that occur over time intervals equal to or smaller than 7 seconds (i.e., variations at frequencies higher than approximately 0.15 Hz), with the variations in the RR intervals occurring over longer intervals then being reflected by computation of the variance of those mean values. FIG. 2C illustrates the frequency response of the $[SD_7]^2$ statistic which shows capture of those frequency components of the RR interval signal from some frequency above DC (since a variance calculation eliminates the DC component of a signal) to approximately ⅐ or 0.15 Hz (i.e., a frequency with a period equal to the length of the 7-second segment). The $SD_{25}$ statistic is similarly defined as the standard deviation of the mean values of all successive 25-second segments in the RR time series, where $[SD_{25}]^2$ is the square of that standard deviation or variance. FIG. 2D illustrates the frequency response of the $[SD_{25}]^2$ statistic which shows capture of those frequency components of the RR interval signal from some frequency above DC to approximately 1/25 or 0.04 Hz (i.e., a frequency with a period equal to the length of the 25-second segment). If the $[SD_{25}]^2$ statistic is subtracted from the $[SD_7]^2$ statistic, the resulting parameter captures a frequency range of heart rate variability which is similar to the LF band illustrated in FIG. 2A.

The rMSSD, $[SD_{25}]^2$, and $[SD_7]^2$ statistics may thus serve as surrogates for the frequency components of an RR time series. An estimate of the LF/HF ratio may then be computed as:

$$\text{Estimated } LF/HF = K\{[SD_7]^2 - [SD_{25}]^2\}/[rMSSD]^2$$

where K is a constant. A linear regression analysis may be performed in which the estimated values are correlated with the actual spectrum of an RR time series to derive the value of K. Alternatively, the estimated LF/HF ratio may be compared with appropriately scaled threshold values in order to assess the autonomic balance of a subject, which eliminates the need for K in the calculation. As described in more detail below, estimating the LF/HF ratio in this manner is much less computationally intensive than direct spectral analysis since the statistical surrogates for frequency content can be computed by maintaining cumulative sums or counts of functions of the measured RR intervals.

A description of an embodiment of the method for estimating an LF/HF ratio and assessing a subject's autonomic balance using statistical surrogates which may be implemented by an implantable device is as follows. The device measures RR intervals between each pair of successive ventricular senses over a predetermined long-term period (e.g., 24 hours) to result in RR interval measurements of an RR time series $RR_1$ through $RR_N$ where N is the total number of RR interval measurements during the predetermined long-term period. Mean values $M_{x1}$ through $M_{xL}$ of successive x-second segments of the RR time series are computed, where x is a predetermined number (e.g., 7) and L is the total number of such x-second segments in the RR time series. Mean values $M_{y1}$ through $M_{yK}$ of successive y-second segments of the RR time series also computed, where y is a predetermined number greater than x (e.g., 25) and K is the total number of such y-second segments in the RR time series. Variances of the mean values $M_{x1}$ through $M_{xL}$ and of the mean values $M_{y1}$ through $M_{yK}$ are next computed, referred to as $[SD_x]^2$ and $[SD_y]^2$, respectively. A mean value of squared successive differences between the RR intervals in the RR time series is next computed to give the $[rMSSD]^2$ parameter. The ratio of the low frequency content in the RR time series between approximately 1/x Hz and 1/y Hz and higher frequency content in the RR time series, referred to as LF/HF, can then be calculated as:

$$LF/HF = K([SD_x]^2 - [SD_y]^2)/[rMSSD]^2$$

where K is a defined constant and LF/HF is taken to be reflective of the subject's autonomic balance with appropriate selection of the x and y values.

In order to compute the statistics, a histogram technique may be employed where cumulative counts of particular functions of the RR interval measurements are maintained. For example, to compute the $[SD_x]^2$ statistic, an integral number T of interval bins $A_1$ through $A_T$ representing interval values $I_1$ through $I_T$ are defined. Each computed mean value $M_{x1}$ through $M_{xL}$ of the successive x-second segments of the RR time series is then assigned to a corresponding one of the interval bins $A_1$ through $A_T$. That is, each computed mean value is assigned to the bin representing an interval value to which it is closest to thereby maintain a cumulative count of the values taken on by the computed mean values. The number of computed mean values assigned to each interval bin $A_1$ through $A_T$ is counted and divided by L to derive a relative frequency $FX_i$ for each interval value $I_i$. $[SD_x]^2$ may then be computed as:

$$[SD_x]^2 = \Sigma(I_i)^2 FX_i - (\Sigma(I_i)FX_i)^2$$

where the summations are carried out from i=1 to T.

The $[SD_y]^2$ statistic may be similarly computed. An integral number S of interval bins $B_1$ through $B_S$ representing interval values $I_1$ through $I_S$ are defined. Each computed mean value $M_{y1}$ through $M_{yK}$ of the successive x-second segments of the RR time series is then assigned to a corresponding one of the interval bins $B_1$ through $B_S$. The number of computed mean values assigned to each interval bin $B_1$ through $B_S$ is counted and divided by K to derive a relative frequency $FY_i$ for each interval value $I_i$. The $[SD_y]^2$ may then be computed as $$[SD_y]^2 = \Sigma(I_i)^2 FY_i - (\Sigma(I_i)FY_i)^2$$

where the summations are carried out from i=1 to S.

A histogram technique may also be used to calculate the $[rMSSD]^2$ statistic. An integral number W of RR interval difference bins $C_1$ through $C_W$ representing RR interval difference values $D_1$ through $D_W$ are defined. An interval difference between each pair of RR intervals in the RR time series is computed as $(RR_2-RR_1)$ through $(RR_N-RR_{N-1})$. Each of the computed interval differences between RR intervals in the RR time series is then assigned to a corresponding one of the RR interval difference bins $C_1$ through $C_W$, and the number of computed interval differences assigned to each RR interval difference bin $C_1$ through $C_W$ is divided by N−1 to derive a relative frequency $FD_i$ for each interval difference $D_i$. The $[rMSSD]^2$ is then computed as:

$$[rMSSD]^2 = \Sigma(D_i)^2 FD_i$$

where the summation is carried out from i=1 to W.

Alternatively, the statistics may be computed by cumulatively summing functions of the RR interval differences. For example, the $[SD_x]^2$ statistic may be computed by cumulatively summing each computed mean value $M_{xi}$ and cumulatively summing each computed mean value $M_{xi}$ squared so that $[SD_x]^2$ may be computed as:

$$[SD_x]^2 = (1/L)\Sigma(M_{xi})^2 - ((1/L)\Sigma M_{xi})^2$$

where the summations are carried out from i=1 to L by the cumulative summing operations. Similarly, the $[SD_y]^2$ statistic may be computed by cumulatively summing each computed mean value $M_{yi}$ and cumulatively summing each computed mean value $M_{yi}$ squared so that $[SD_y]^2$ may be computed as:

$$[SD_y]^2 = (1/L)\Sigma(M_{yi})^2 - ((1/L)\Sigma M_{yi})^2$$

where the summations are carried out from i=1 to K by the cumulative summing operations. The $[rMSSD]^2$ statistic may be computed by cumulatively summing each computed interval difference value $(RR_{i+1} - RR_i)$ squared and then computing $[rMSSD]^2$ as:

$$[rMSSD]^2 = (1/(N-1))\Sigma(RR_{i+1} - RR_i)^2$$

where the summation is carried out from i=1 to N-1 by the cumulative summing operation.

As noted earlier, investigators have generally found that the optimum frequency ranges for computation of the LF/HF ratio in order to assess autonomic balance is with an LF band between 0.04 Hz and 0.15 Hz and with an HF band between 0.15 Hz and 0.40 Hz. This would correspond to x and y values in the above description of 7 and 25, respectively. Different LF and HF frequency ranges and/or different x and y values, however, may be found to more optimally assess autonomic balance in a particular patient. Also, a standard long-term period over which to define an RR time series is 24 hours, but a different long-term period may be more appropriate in certain circumstances. In another embodiment of the method, a moving average of estimated LF/HF ratios over successive long-term time periods may be computed.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for operating an implantable medical device in order to assess a subject's autonomic balance, comprising:
    sensing electrical activity in a ventricle and generating a ventricular sense signal when the sensed electrical activity exceeds a predetermined threshold;
    measuring time intervals between each pair of successive ventricular senses, referred to as RR intervals, over a predetermined long-term period, where N is the total number of RR interval measurements during the predetermined long-term period and the measured RR intervals $RR_1$ through $RR_N$ are referred to as an RR time series;
    computing mean values $M_{x1}$ through $M_{xL}$ of successive x-second segments of the RR time series, where x is a predetermined number and L is the total number of such x-second segments in the RR time series, and computing a variance of the mean values $M_{x1}$ through $M_{xL}$, referred to as $[SD_x]^2$;
    computing mean values $M_{y1}$ through $M_{yK}$ of successive y-second segments of the RR time series, where y is a predetermined number greater than x and K is the total number of such y-second segments in the RR time series, and computing a variance of the mean values $M_{y1}$ through $M_{yK}$, referred to as $[SD_y]^2$;
    computing a mean value of squared successive differences between the RR intervals in the RR time series, referred to as $[rMSSD]^2$; and,
    estimating a ratio of the low frequency content in the RR time series between approximately 1/x Hz and 1/y Hz and higher frequency content in the RR time series, referred to as LF/HF, as:

$$LF/HF = K([SD_x]^2 - [SD_y]^2)/[rMSSD]^2$$

wherein K is a defined constant and LF/HF is reflective of the subject's autonomic balance.

2. The method of claim 1 further comprising:
    defining an integral number T of RR interval bins $A_1$ through $A_T$ representing RR interval values $I_1$ through $I_T$;
    assigning each computed mean value $M_{x1}$ through $M_{xL}$ of the successive x-second segments of the RR time series to a corresponding one of the RR interval bins $A_1$ through $A_T$;
    counting the number of computed mean values assigned to each RR interval bin $A_1$ through $A_T$ and dividing each such number by L to derive a relative frequency $FX_i$ for each interval value $I_i$; and,
    computing $[SD_x]^2$ as $$[SD_x]^2 = \Sigma(I_i)^2 FX_i - (\Sigma(I_i) FX_i)^2$$

where the summations are carried out from i=1 to T.

3. The method of claim 1 further comprising:
    defining an integral number S of RR interval bins $B_1$ through $B_S$ representing RR interval values $I_1$ through $I_S$;
    assigning each computed mean value $M_{y1}$ through $M_{yK}$ of the successive y-second segments of the RR time series to a corresponding one of the RR interval bins $B_1$ through $B_S$;
    counting the number of computed mean values assigned to each RR interval bin $B_1$ through $B_S$ and dividing each such number by K to derive a relative frequency $FY_i$ for each interval value $I_i$; and,
    computing $[SD_y]^2$ as $$[SD_y]^2 = \Sigma(I_i)^2 FY_i - (\Sigma(I_i) FY_i)^2$$

where the summations are carried out from i=1 to S.

4. The method of claim 1 further comprising:
    defining an integral number W of RR interval difference bins $C_1$ through $C_W$ representing RR interval difference values $D_1$ through $D_W$;
    computing an interval difference between each pair of RR intervals in the RR time series as $(RR_2 - RR_1)$ through $(RR_N - RR_{N-1})$;
    assigning each of the computed interval differences between RR intervals in the RR time series to a corresponding one of the RR interval difference bins $C_1$ through $C_W$;
    counting the number of computed interval differences assigned to each RR interval difference bin $C_1$ through $C_W$ and dividing each such number by N-1 to derive a relative frequency $FD_i$ for each interval difference $D_i$; and,
    computing $[rMSSD]^2$ as $$[rMSSD]^2 = \Sigma(D_i)^2 FD_i$$

where the summation is carried out from i=1 to W.

5. The method of claim 1 further comprising:
    cumulatively summing each computed mean value $M_{xi}$;
    cumulatively summing each computed mean value $M_{xi}$ squared;
    computing $[SD_x]^2$ as:

$$[SD_x]^2 = (1/L)\Sigma(M_{xi})^2 - ((1/L)\Sigma M_{xi})^2$$

where the summations are carried out from i=1 to L by the cumulative summing operations.

6. The method of claim 1 further comprising:
cumulatively summing each computed mean value $M_{yi}$;
cumulatively summing each computed mean value $M_{yi}$ squared;
computing $[SD_y]^2$ as:

$$[SD_y]^2 = (1/L)\Sigma(M_{yi})^2 - ((1/L)\Sigma M_{yi})^2$$

where the summations are carried out from i=1 to K by the cumulative summing operations.

7. The method of claim 1 further comprising:
cumulatively summing each computed interval difference value $(RR_{i+1} - RR_i)$ squared;
computing $[rMSSD]^2$ as:

$$[rMSSD]^2 = (1/(N-1))\Sigma(RR_{i+1} - RR_i)^2$$

where the summation is carried out from i=1 to N-1 by the cumulative summing operation.

8. The method of claim 1 wherein the predetermined long-term period is 24 hours.

9. The method of claim 1 wherein the predetermined numbers x and y are 7 and 25, respectively, such that the estimated LF/HF represents a ratio of the low frequency content in the RR time series between approximately 0.04 Hz and 0.15 Hz and the high frequency content in the RR time series between approximately 0.15 Hz and 0.4 Hz.

10. The method of claim 1 further comprising computing a moving average of estimated LF/HF ratios over successive long-term time periods.

11. A cardiac rhythm management device, comprising:
a sensing channel for sensing electrical activity in a ventricle;
a controller interfaced to the sensing channel which detects a ventricular sense when the sensed electrical activity exceeds a predetermined threshold;
wherein the controller is programmed with executable instructions for:
measuring time intervals between each pair of successive ventricular senses, referred to as RR intervals, over a predetermined long-term period, where N is the total number of RR interval measurements during the predetermined long-term period and the measured RR intervals $RR_1$ through $RR_N$ are referred to as an RR time series;
computing mean values $M_{x1}$ through $M_{xL}$ of successive x-second segments of the RR time series, where x is a predetermined number and L is the total number of such x-second segments in the RR time series, and computing a variance of the mean values $M_{x1}$ through $M_{xL}$, referred to as $[SD_x]^2$;
computing mean values $M_{y1}$ through $M_{yK}$ of successive y-second segments of the RR time series, where y is a predetermined number greater than x and K is the total number of such y-second segments in the RR time series, and computing a variance of the mean values $M_{y1}$ through $M_{yK}$, referred to as $[SD_y]^2$;
computing a mean value of squared successive differences between the RR intervals in the RR time series, referred to as $[rMSSD]^2$; and,
estimating a ratio of the low frequency content in the RR time series between approximately 1/x Hz and 1/y Hz and higher frequency content in the RR time series, referred to as LF/HF, as:

$$LF/HF = K([SD_x]^2 - [SD_y]^2)/[rMSSD]^2$$

wherein K is a defined constant and LF/HF is reflective of the subject's autonomic balance.

12. The device of claim 11 wherein the controller is further programmed with instructions for:
defining an integral number T of RR interval bins $A_1$ through $A_T$ representing RR interval values $I_1$ through $I_T$;
assigning each computed mean value $M_{x1}$ through $M_{xL}$ of the successive x-second segments of the RR time series to a corresponding one of the RR interval bins $A_1$ through $A_T$;
counting the number of computed mean values assigned to each RR interval bin $A_1$ through $A_T$ and dividing each such number by L to derive a relative frequency $FX_i$ for each interval value $I_i$; and,
computing $[SD_x]^2$ as $$[SD_x]^2 = \Sigma(I_i)^2 FX_i - \Sigma(I_i)FX_i)^2$$

where the summations are carried out from i=1 to T.

13. The device of claim 11 wherein the controller is further programmed with instructions for:
defining an integral number S of RR interval bins $B_1$ through $B_S$ representing RR interval values $I_1$ through $I_S$;
assigning each computed mean value $M_{y1}$ through $M_{yK}$ of the successive y-second segments of the RR time series to a corresponding one of the RR interval bins $B_1$ through $B_S$;
counting the number of computed mean values assigned to each RR interval bin $B_1$ through $B_S$ and dividing each such number by K to derive a relative frequency $FY_i$ for each interval value $I_i$; and,
computing $[SD_y]^2$ as $$[SD_y]^2 = \Sigma(I_i)^2 FY_i - (\Sigma(I_i)F$$

where the summations are carried out from i=1 to S.

14. The device of claim 11 wherein the controller is further programmed with instructions for:
defining an integral number W of RR interval difference bins $C_1$ through $C_W$ representing RR interval difference values $D_1$ through $D_W$;
computing an interval difference between each pair of RR intervals in the RR time series as $(RR_2 - RR_1)$ through $(RR_N - RR_{N-1})$;
assigning each of the computed interval differences between RR intervals in the RR time series to a corresponding one of the RR interval difference bins $C_1$ through $C_W$;
counting the number of computed interval differences assigned to each RR interval difference bin $C_1$ through $C_W$ and dividing each such number by N-1 to derive a relative frequency $FD_i$ for each interval difference $D_i$; and,
computing $[rMSSD]^2$ as $$[rMSSD]^2 = \Sigma(D_i)^2 FD_i$$

where the summation is carried out from i=1 to W.

15. The device of claim 11 wherein the controller is further programmed with instructions for:
cumulatively summing each computed mean value $M_{xi}$;
cumulatively summing each computed mean value $M_{xi}$ squared;
computing $[SD_x]^2$ as:

$$[SD_x]^2 = \Sigma(1/L)\Sigma(M_{xi})^2 - ((1/L)\Sigma M_{xi})^2$$

where the summations are carried out from i=1 to L by the cumulative summing operations.

16. The device of claim 11 wherein the controller is further programmed with instructions for:
  cumulatively summing each computed mean value $M_{yi}$;
  cumulatively summing each computed mean value $M_{yi}$ squared;
  computing $[SD_y]^2$ as:

$$[SD_y]=(1/L)\Sigma(M_{yi})^2-((1/L)\Sigma M_{yi})^2$$

where the summations are carried out from i=1 to K by the cumulative summing operations.

17. The device of claim 11 wherein the controller is further programmed with instructions for:
  cumulatively summing each computed interval difference value $(RR_{i+1}-RR_i)$ squared;
  computing $[rMSSD]^2$ as:

$$[rMSSD]^2=(1/(N-1))\Sigma(RR_{i+1}-RR_i)^2$$

where the summation is carried out from i=1 to N−1 by the cumulative summing operation.

18. The device of claim 11 wherein the predetermined long-term period is 24 hours.

19. The device of claim 11 wherein the predetermined numbers x and y are 7 and 25, respectively, such that the estimated LF/HF represents a ratio of the low frequency content in the RR time series between approximately 0.04 Hz and 0.15 Hz and the high frequency content in the RR time series between approximately 0.15 Hz and 0.4 Hz.

20. The device of claim 11 wherein the controller is further programmed with instructions for computing a moving average of estimated LF/HF ratios over successive long-term time periods.

* * * * *

UNITED STATES PATENT AND TRADEMARK OFFICE
CERTIFICATE OF CORRECTION

PATENT NO. : 7,069,070 B2
APPLICATION NO. : 10/436876
DATED : June 27, 2006
INVENTOR(S) : Carlson et al.

It is certified that error appears in the above-identified patent and that said Letters Patent is hereby corrected as shown below:

In column 10, line 34, in Claim 13, delete "$(\Sigma(I_i)F$" and insert -- $(\Sigma(I_i)Fy_i)^2$ --, therefor.

In column 10, line 65, in Claim 15, delete "$\Sigma(1/L) \Sigma(M_{xi})^2$" and insert -- $(1/L) \Sigma(M_{xi})^2$ --, therefor.

Signed and Sealed this

Twenty-first Day of November, 2006

JON W. DUDAS
*Director of the United States Patent and Trademark Office*